United States Patent [19]

Tauc et al.

[11] Patent Number: 4,710,030
[45] Date of Patent: Dec. 1, 1987

[54] OPTICAL GENERATOR AND DETECTOR OF STRESS PULSES

[75] Inventors: Jan Tauc; Humphrey J. Maris, both of Barrington; Christian Thomsen, Providence, all of R.I.

[73] Assignee: Bw Brown University Research Foundation, Providence, R.I.

[21] Appl. No.: 735,825

[22] Filed: May 17, 1985

[51] Int. Cl.[4] ............................................. G01N 21/00
[52] U.S. Cl. ..................................... 356/432; 73/643; 374/57; 356/445
[58] Field of Search ...................... 356/32, 432 T, 445; 374/5, 7, 17, 57; 73/655, 760, 800, 643

[56] References Cited

U.S. PATENT DOCUMENTS 4,484,820  11/1984  Rosencwaig ........................... 73/643
4,579,463   4/1986  Rosencwaig et al. ................. 374/5

OTHER PUBLICATIONS

Auston et al., "Picosecond Ellipsometry of Transient Electron-Hole Plasmas in Germanium", *Physical Review Letters*, vol. 32, No. 20, (May 20, 1974), pp. 1120-1123.
Liu et al., "Picosecond Time-Resolved Plasma and Temperature-Induced Changes of Reflectivities and Transmission in Silicon", *Appl. Phys. Lett.*, vol. 41, No. 7, (Oct. 1, 1982), pp. 643-646.
Shay, "Photoreflectance Line Shape at the Fundamental Edge in Ultrapure GaAs", *Physical Review B*, vol. 2, No. 4, (Aug. 15, 1970), pp. 803-807.
Nilsson, "Reflectance Modulation in Ge and GeAs by Optical Carrier Injection", *Solid State Communications*, vol. 7, No. 5, (1969), pp. 479-481.
Thomsen et al., "Coherent Phonon Generation and Detection by Picosecond Light Pulses", *Physical Review Letter*, vol. 53, No. 10, (Sep. 3, 1984), pp. 989-992.
Thomsen et al., "Picosecond Optical Generation and Detection of Phonon Waves in a-As$_2$Te$_3$", *AIP Conference Proceedings No. 120*, Optical Effects in Amorphous Semiconductors, pp. 102-109, (1984).
Thomsen et al., "Picosecond Optical Excitation of Phonons in Amorphous As$_2$Te$_3$" *Ultrafast Phenomena IV*, ed. Austron et al., Springer Verlag, New York, 1984, pp. 133-136.
Downer et al., "Imaging with Feutosecond Optical Pulses", *Ultrafast Phenomena IV*, Springer Verlag, New York, 1984, pp. 106-110.
Rosencwaig et al., "Detection of Thermal Waves through Optical Reflectance", *Applied Physics Letters*, 46(11), Jun. 1, 1985, pp. 1013-1015.

*Primary Examiner*—R. A. Rosenberger
*Attorney, Agent, or Firm*—Joseph S. Iandiorio; Douglas E. Denninger

[57] ABSTRACT

An optical stress pulse generation and detection system for non-destructively measuring physical properties of a sample, which uses a pump beam having short duration radiation pulses having an intensity and at least one wavelength selected to non-destructively generate a stress pulse in a sample and directs the non-destructive pump beam to a surface of the sample to generate the stress pulse. The optical stress pulse generation and detection system also uses a probe radiation beam and guides the probe beam to a location at the sample to intercept the stress pulse. The change in optical constants induced by the stress pulse is detected by observing the probe beam after it intercepts the stress pulse.

37 Claims, 15 Drawing Figures

OPTICAL GENERATOR AND DETECTOR OF STRESS PULSES

FIELD OF INVENTION

This invention relates to a system for measuring properties of thin films, and more particularly to a system which optically induces stress pulses in a film and optically measures the pulses after they have travelled through the film.

BACKGROUND OF INVENTION

Presently, thin films are studied using a number of techniques. In one ultrasonic technique, a radio frequency pulse is applied to a piezoelectric transducer mounted on a substrate between the transducer and the film to be studied. A stress pulse propagates through the substrate toward the film. At the boundary between the substrate and the film, part of the pulse is reflected back to the transducer. The remainder enters the film and is partially reflected at the opposite side to return through the substrate to the transducer. The pulses are converted into electrical signals, amplified electronically, and displayed on an oscilloscope. The time delay between the two pulses indicates the film thickness, if the sound velocity in the film is known, or indicates the sound velocity, if the film thickness is known. Relative amplitudes of the pulses provide information on the attenuation in the film or the quality of the bond between the film and the substrate.

The minimum thickness of films which can be measured using ultrasonics is limited by the pulse length. The duration of the stress pulse is normally 0.1 $\mu$sec corresponding to a spatial length of at least $3 \times 10^{-2}$ cm for an acoustic velocity of $3 \times 10^5$ cm/sec. Unless the film is thicker than the length of the acoustic pulse, the pulses returning to the transducer will overlap in time. Even if pulses as short in duration as 0.001 $\mu$sec are used, the film thickness must be at least a few microns.

Another technique, acoustic microscopy, projects sound through a rod having a spherical lens at its tip. The tip is immersed in a liquid covering the film. Sound propagates through the liquid, reflects off the surface of the sample, and returns through the rod to the transducer. The amplitude of the signal returning to the transducer is measured while the sample is moved horizontally. The amplitudes are converted to a computer-generated photograph of the sample surface. Sample features below the surface are observed by raising the sample to bring the focal point beneath the surface. The lateral and vertical resolution of the acoustic microscope are approximately equal.

Resolution is greatest for the acoustic microscope when a very short wavelength is passed through the coupling liquid. This requires a liquid with a low sound velocity, such as liquid helium. An acoustic microscope using liquid helium can resolve surface features as small as 500 Angstroms, but only when the sample is cooled to 0.1° K.

Several additional techniques not involving generation and detection of stress pulses are available for measuring film thickness. Ellipsometers direct elliptically polarized light at a film sample and analyze the polarization state of the reflected light to determine film thickness with an accuracy of 3-10 Angstroms. The elliptically polarized light is resolved into two components having separate polarization orientations and a relative phase shift. Changes in polarization state, beam amplitudes and phase of the two polarization components after reflection are observed.

The ellipsometer technique requires films which are reasonably transparent. Typically, at least 10% of the polarized radiation must pass through the film. The thickness of metal sample films thus cannot exceed a few hundred Angstroms.

Another technique uses a small stylus to mechanically measure film thickness. The stylus is moved across the surface of a substrate and, upon reaching the edge of a sample film, measures the difference in height between the substrate and the film. Accuracies of 10-100 Angstroms can be obtained. This method cannot be used if the film lacks a sharp, distinct edge or is too soft in consistency to accurately support the stylus.

Another non-destructive method, based on Rutherford Scattering, measures the energy of backscattered helium ions. The lateral resolution of this method is poor.

Yet another technique uses resistance measurements to determine film thickness. For a material of known resistivity the film thickness is determined by measuring the electrical resistance of the film. For films less than 1000 Angstroms, however, this method is of limited accuracy because the resistivity may be non-uniformly dependent on the film thickness.

In yet another technique, the change in the direction of a reflected beam off a surface is studied when a stress pulse arrives at the surface. In a particular application, stress pulses are generated by an ultrasonic transducer on one side of a film to be studied. A laser beam focused onto the other side detects the stress pulses after they traverse the sample. This method is useful for film thicknesses greater than 10 microns.

A film may also be examined by striking a surface of the film with an intense optical pump beam to disrupt the film's surface. Rather than observe propagation of stress pulses, however, this method observes destructive excitation of the surface. The disruption, such as thermal melting, is observed by illuminating the site of impingement of the pump beam with an optical probe beam and measuring changes in intensity of the probe beam. The probe beam's intensity is altered by such destructive, disruptive effects as boiling of the film's surface, ejection of molten material, and subsequent cooling of the surface. See Downer, M. C.; Fork, R. L.; and Shank, C. V., "Imaging with Femtosecond Optical Pulses", *Ultrafast Phenomena IV*, Ed. D. H. Auston and K. B. Eisenthal (Spinger-Verlag, N.Y. 1984), pp. 106-110.

Other systems measure thickness, composition or concentration of material by measuring absorption of suitably-chosen wavelengths of radiation. This method is applicable only if the film is on a transparent substrate.

SUMMARY OF INVENTION

It is therefore an object of this invention to provide an improved system for measuring physical properties of a film which generates a stress pulse and detects stress-induced changes in the optical constants of the film.

It is a further object of this invention to provide such a system in which both generation and detection of stress pulses are performed optically.

It is a further object of this invention to provide such a system which measures non-destructively.

It is a further object of this invention to provide such a system which can measure very thin films.

It is a further object of this invention to provide such a system which can study areas of a film at least as small as 1 micron square.

It is a further object of this invention to provide such a system which is not limited by the transparency of the film to be measured.

It is a further object of this invention to provide such a system which measures films independent of their characteristic wavelength absorptions.

It is a further object of this invention to provide such a system which is not limited by the consistency of the film.

It is a further object of this invention to provide such a system which operates over a wide range of temperature.

It is a further object of this invention to provide such a system which does not make mechanical contact with the film.

The invention results from the realization that a truly effective instrument for measuring physical properties of a film can be achieved by optically generating stress pulses in the film and optically detecting changes in optical constants representative of the induced stress pulses.

This invention features an optical generation and detection system for non-destructively measuring physical properties of a sample. There is a radiation source for providing a pump beam having short duration radiation pulses having an intensity and at least one wavelength selected to non-destructively generate a stress pulse in the sample, a radiation source for providing a probe beam, means for directing the pump beam to a surface of the sample to generate the stress pulse in the sample, and means for guiding the probe beam to a location at the sample to intercept the stress pulse. There is also means responsive to the probe beam for detecting the change in optical constants induced by the stress pulse in the sample.

In one embodiment, the means for detecting includes means for measuring the intensity of the reflected or transmitted probe beam. The pump beam and probe beam are derived from the same source beam having a plurality of short duration pulses, and the stress pulse detector further includes beam splitting means for directing a first portion of the source beam to form the pump beam, having the plurality of pulses, and directing a second portion to form the probe beam, also having the plurality of pulses. The source beam has a single direction of polarization and the stress pulse detector further includes means for rotating the direction of polarization of the probe beam and means, disposed between the test sample and the means for detecting, for transmitting only radiation at the rotated direction of polarization. The stress pulse detector may further include chopper means for modulating the pump beam at a predetermined frequency and amplifier means, responsive to the chopper means, for amplifying only the output of the means for measuring corresponding to the predetermined frequency. The means for guiding includes means for setting a predetermined time delay between the impingement of a pulse of the pump beam and a pulse of the probe beam upon the sample. The means for detecting includes means for averaging the output of the means for measuring for a plurality of pulse detections while the delay between impingements remains set at the predetermined time delay. The means for setting may sequentially change the predetermined time delay and the means for averaging may successively average the output of the means for measuring during each successive predetermined time delay setting. The pump beam receives 50–99% of the source beam and the source beam has an average power of $10\mu$ to 1 kW. The source beam includes wavelengths from 100 Angstroms to 100 microns and the radiation pulses of the source beam have a duration of 0.01 to 100 psec.

The test sample may include a substrate and a film to be examined disposed on the substrate to define a boundary between them. For an optically opaque film, the pump beam and the probe beam may impinge on the surface of the film opposite the boundary. For an optically opaque film and an optically transparent substrate, the probe beam and the pump beam may travel through the substrate to impinge upon the boundary. Alternatively, one beam travels through the transparent substrate to impinge upon the boundary and the other beam impinges upon the surface opposite the boundary. For an optically transparent film and an optically opaque substrate, the pump beam and probe beam may travel through the film to impinge upon the boundary. The substrate may be an opto-acoustically active medium, or the test sample may further include an opto-acoustically active medium disposed on the surface of the film opposite the boundary, and the pump beam and probe beam may impinge upon the active medium. The film may have a thickness from 50 Angstroms to 100 microns. The probe beam source may provide a continuous radiation beam and the pump beam source may provide at least one discrete pump pulse and may provide pulses having a duration of 0.01 to 100 psec and an average power of $10\,\mu W$ to 1 kW. Alternatively, the probe beam source provides probe beam pulses having a duration of 0.01 to 100 psec and the pump beam source provides pump beam pulses having a duration of 0.01 to 100 psec. The pump beam and the probe beam may impinge upon the same location at the sample, and the means for directing and the means for guiding may include a common lens system for focussing the pump beam and the probe beam onto the sample. The position of impingement of the probe beam may be shifted relative to that of the pump beam and the probe beam may be transmitted or reflected by the sample.

This invention also features a method for optically and non-destructively generating and detecting the propagation of a stress pulse in a test sample including producing a pump beam having short duration radiation pulses having an intensity and at least one wavelength selected to non-destructively generate a stress pulse in the sample, producing a probe radiation beam, directing the pump beam to a surface of the sample to generate the stress pulse in the sample, and guiding the probe beam to a location at the sample to intercept the stress pulse. The method further includes detecting the change in optical constants induced by the stress pulse by measuring the intensity of the probe beam after it intercepts the stress pulse. Also featured is a method including producing a source beam having short duration pulses of radiation, diverting a first portion of the source beam to form a pump beam having an intensity and at least one wavelength selected to non-destructively generate a stress pulse in the sample, diverting a second portion of the source beam to form a probe beam, directing the pump to a surface of a test sample to generate a stress pulse in the sample, guiding the probe beam to a location at the sample to intercept the stress pulse, and detecting the change in optical constants induced by the stress pulse.

DISCLOSURE OF PREFERRED EMBODIMENT

Other objects, features and advantages will occur from the following description of a preferred embodiment and the accompanying drawings, in which.

This invention may be accomplished by an optical generator and detector of stress pulses, hereinafter referred to as an optical stress pulse generation and detection system, in which a non-destructive pulsed beam of electromagnetic radiation is directed upon a film to be examined to produce a stress pulse in the film, and in which an optical probe beam is directed upon the film such that the intensity of the reflected or transmitted probe beam is affected by changes, induced by the stress pulse, in the optical constants of the film. Physical properties of the film are measured by observing the changes in reflected or transmitted probe beam intensity, or in stress pulse travel time as revealed by the changes in intensity. Optical stress pulse generation and detection systems according to this invention can dramatically shorten the time scale required by conventional devices for inducing stress pulses and studying their propagation. The shortened time scale is particularly important for studying films less than 10 microns in thickness.

Figure 1A:
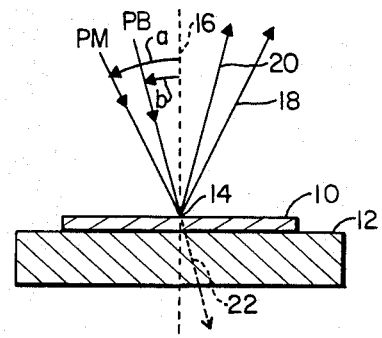
FIG. 1A is an illustration of a film to be examined by a pump beam and a probe beam according to this invention.
Figure 1B:
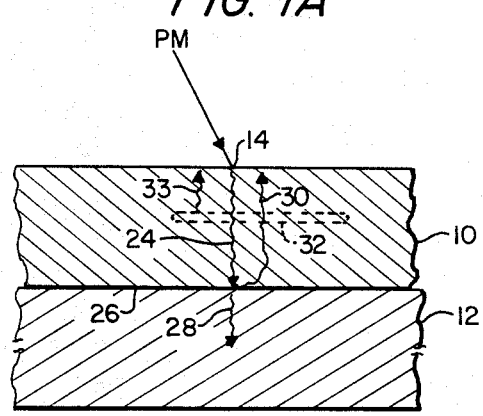
FIG. 1B is an enlarged, more detailed view of a portion of FIG. 1A.

The arrangement of the pump beam and a probe beam according to this invention is illustrated in FIGS. 1A and 1B. Film 10 is shown in FIG. 1A mounted on substrate 12. To test film 10, pump beam PM is directed to position 14 on film 10 to induce a stresspulse in the film. The stress pulse is a stress wave, also known as an acoustic phonon. Pump beam PM is incident on film 10 at angle a from normal 16. A portion of pulsed beam PM is absorbed by film 10; the unabsorbed, reflected portion is represented by departing beam 18. Probe beam PB is directed to position 14 at angle b to intercept returning stress pulses from the induced stress pulse. The actual values of angles a and b can be selected from a wide range of angles. The intensity of beam PB reflected as beam 20 or transmitted as beam 22 depends on the optical constants of film 10 as affected by the stress pulse. The optical constants are the index of refraction and the absorption coefficient. The use of opaque versus transparent substrates and the arrangement of the film and the substrate are described below.

The stress pulse produced by the absorption of pump beam PM is illustrated in FIG. 1B. The radiation pulse of pump beam PM when striking position 14 produces stress in the upper layers of film 10. Under typical conditions the film absorbs a pump radiation pulse within several hundred Angstroms of its surface. The radiation pulse heats and expands the film, generating an acoustic wave, hereinafter referred to as a stress pulse. Other interactions, such as changes in the distribution of electrons, may contribute to stress in the film.

As shown in FIG. 1B, pump beam PM strikes film 10 at position 14 to generate stress pulse 24. Stress pulse 24 travels away from position 14 toward boundary 26 between film 10 and substrate 12. Depending on the physical characteristics of substrate 12, a portion of stress pulse 24 enters substrate 12 as pulse 28; other portions of stress pulse 24 are reflected from boundary 26 to return as pulse 30 to the upper surface of film 10. When a reflected probe beam is monitored, the intensity of the probe beam changes whenever a portion of the induced stress pulse returns to the surface of the film and affects the optical constants of the film at the surface. As described below, the rate of travel of stress pulses 24 and 30 and their intensity provides information on sound velocity, sound attenuation, the bonding of the film to the substrate, and film thickness. Voids, cracks, or heterogeneities in composition, such as the defect 32, shown in phantom, produce additional stress pulses such as pulse 33.

Figure 2:
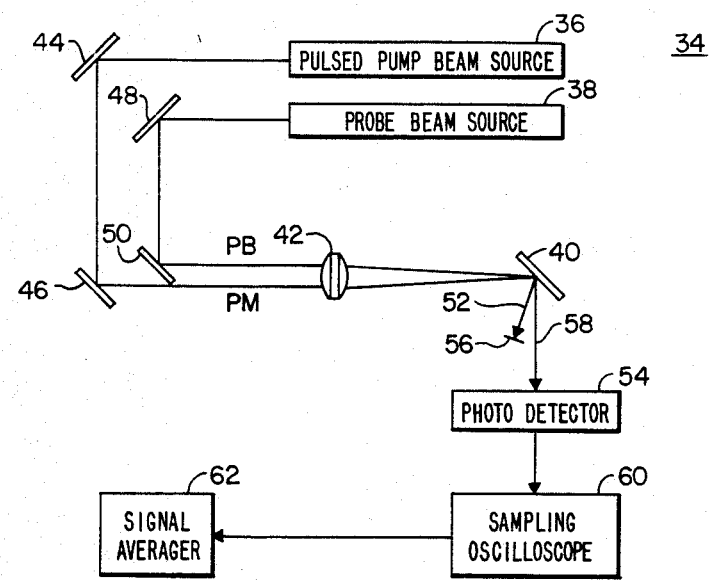
FIG. 2 is a schematic diagram of an optical stress pulse generation and detection system according to this invention.

Optical stress pulse generation and detection system 34, FIG. 2, includes radiation source 36 for providing pulsed pump beam PM and radiation source 38 for providing a continuous probe beam PB. The term radiation is intended to include more than visible light, such as ultraviolet and infrared radiation. The wavelength of the pump beam PM should be selected so that it is strongly absorbed in the particular film to be studied or in a medium associated with the film, as described below. Radiation meeting this absorption criterion can be selected from wavelengths of 100 Angstroms to 100 microns. Pump beam PB preferably is pulsed at an average power of 10 $\mu$W to 1 kW and a repetition rate of 1 Hz to 10 GHz, each pulse having a duration of 0.01 psec to 100 psec. Pump beam PM and probe beam PB are directed to film 40 through lens 42. Acceptable thicknesses of film 40 range from 50 Angstroms to 100 microns. Mirrors 44, 46 and 48, 50 direct pump beam PM and probe beam PB, respectively, to lens 42. The portion of pump beam PM that is not absorbed by film 40 is reflected as ray 52 and prevented from reaching photodetector 54 by beam-blocker 56. When the induced stress pulse returns to the surface of film 40 it causes a slight variation in reflectivity which changes the intensity of reflected ray 58 of continuous probe beam PB. Photodetector 54, such as a PD 15 available from Opto-Electronics, Inc., has a sufficiently short response time to respond to the fast changes in reflectivity. The output of detector 54 is displayed in sampling oscilloscope 60 as a function of time. Signal averager 62, interfaced with oscilloscope 60, integrates the responses over many pump beam pulses and improves the signal-to-noise ratio.

Optical stress pulse generation and detection system 34 can also operate with a single pump pulse (single-shot) and a continuous probe beam. In this case sampling oscilloscope 60 and signal averager 62 are replaced by a transient signal recorder, such as a model 6500 available from Biomation Inc. One pump pulse is provided for each observation period. An observation period consists of monitoring changes in intensity of the continuous probe beam during and after the "single shot" is fired.

Figure 3:
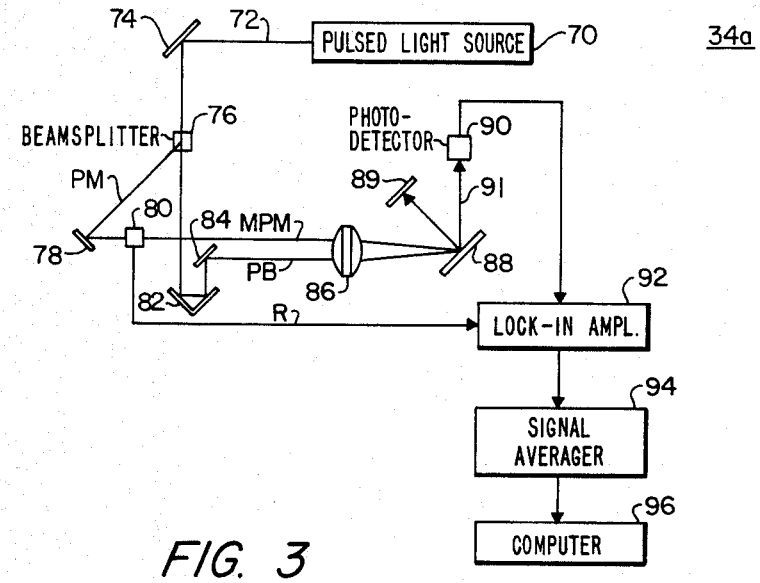
FIG. 3 is a schematic diagram of another arrangement of an optical stress pulse generation and detection system according to this invention.

For films having a thickness less than 5 microns a different configuration of the optical generator and detector of stress pulses may be used; presently this alternate method must be used to measure films of thickness less than 0.1 micron. Optical stress pulse generation and detection system 34a, FIG. 3, can observe events in the picosecond range using a pulsed probe beam. Source beam 72, having an average power of 10 $\mu$W to 1 kW, a repetition rate of 1 Hz to 10 GHz and a duration of 0.01 psec to 100 psec, from light source 70 is directed by mirror 74 through beam splitter 76. At beam splitter 76, a portion of source beam 72 becomes pump beam PM, which is directed by mirror 78 to chopper 80. Chopper 80 imparts a modulation to pump beam PM that is several orders of magnitude longer in duration than a pulse of beam 72. Thus, chopper 80 permits a series of pump pulses to impinge upon film 88 during one period and then blocks a series of pump pulses during the next period.

Beam splitter 76 directs a smaller portion of beam 72 to corner cube mirror 82. The distance between mirror 84 and corner cube 82 is varied to vary the delay between impingement of probe beam PB and pump beam PM at film 88. The effect of this predetermined time delay is discussed below.

Pump beam PM and probe beam PB pass through lens 86 where they are focussed on the same spot of film 88. The reflected portion of pump beam PM is halted by beam-blocker 89. Detector 90 detects the change in intensity of reflected probe beam 91 as the optical constants of film 88 are changed by the induced stress pulse. Lock-in amplifier 92 accepts and amplifies signals from detector 90 that match only the frequency and phase of chopper 80, as provided by reference signal R to lock-in amplifier 92. Probe beam PB is not modulated by chopper 80 but acquires changes in intensity according to this modulation rate. Each series of pump pulses allowed through chopper 80 induces a corresponding series of stress pulses in film 88 which in turn induce changes in the optical constants. Changes in the optical constants alter the intensity of reflected probe beam 91 during each series. Alterations in intensity of reflected probe beam 91 that occur at other than the frequency of chopper 80 are rejected by amplifier 92.

Lock-in amplifier 92 provides a single voltage output proportional to the difference between the original intensity of beam 91 when film 88 is under illumination of pump beam PB and when it is not under illumination. Signals received by lock-in amplifier 92 are averaged over time by signal averager 94 and transferred to computer 96 for storage and analysis.

Figure 4:
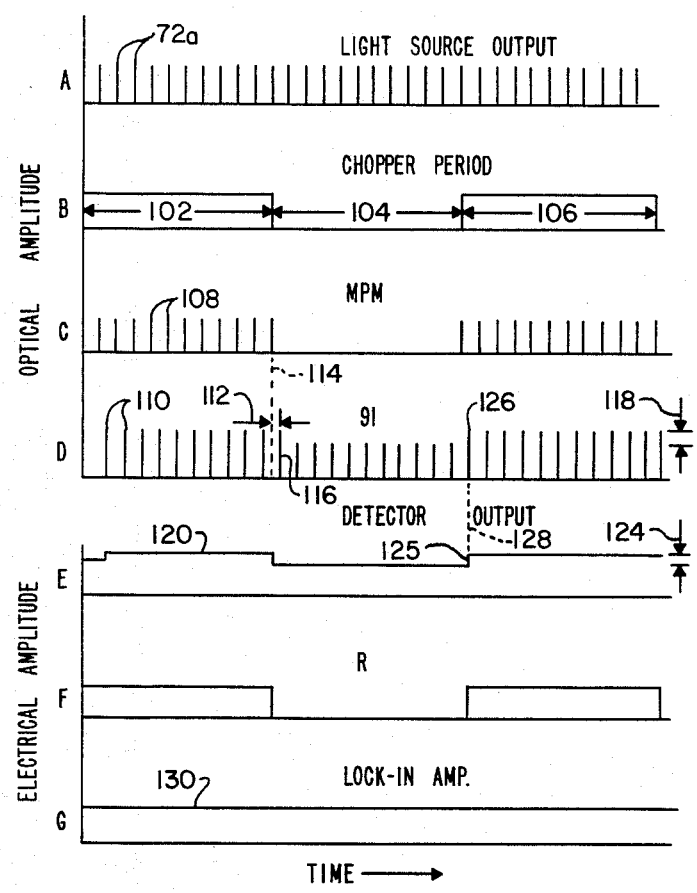
FIG. 4 is a set of timing diagrams for the optical and electrical wave forms occurring in the system of FIG. 3.

Examples of acceptable timings for the optical and electrical waveforms utilized by optical stress pulse generation and detection system 34a are shown as timing diagrams in FIG. 4. Pulses 72a, chart A, have a duration of 0.2 psec and a period of 11 nsec between pulses as provided by light source 70. Chopper 80 modulates the light source output at 125 nsec intervals 102, 104, and 106, chart B. Pulses 108, chart C, of modulated pump beam MPM exhibit the 11 nsec period of source pulses 72a during chopper periods 102, 106. No pump beam pulses are impinging on the sample during time interval 104. Incident pulses of probe beam, Chart D, have the same 11 nsec periodicity of pump pulses 72a, but are delayed relative to the pump pulses by the extent indicated by arrow 112 between dotted line 114 and probe pulse 116. This delay is between 0 and 2 nsec. The probe pulses do not pass through the chopper, and therefore impinge on the film surface with constant intensity. After reflection the probe pulses have a different intensity in time intervals 102 and 104 as shown by arrow 118. This difference is caused by the changes in reflectivity produced by the stress pulses in the sample generated by the pump. Increment 118 is quite small: the intensity of probe beams 91 is between 1 and 50% of source beam 72a and increment 118 is approximately $10^{-4}$ to $10^{-5}$ of the intensity of probe beam 91.

Output 120 of the photodetector 90, chart E, is an envelope of reflected pulses of probe beam 91 having an increment 124 corresponding to increment 118. Increases in detector output 120 correspond to increases in pulse intensity of probe beam 91, such as rise 125 corresponding to pulse 126. The correlation is indicated by dashed line 128.

Output 130 of lock-in amplifier 94 is proportional to increment 124. The chopper period, chart B, is provided to the lock-in amplifier as electrical signal R, chart F. Output 130 of lock-in amplifier 92 is recorded using signal averager 94, FIG. 3, as a function of the delay between the probe and pump pulses generated by a translation stage, described below, which controls corner cube mirror 82.

Figure 5:
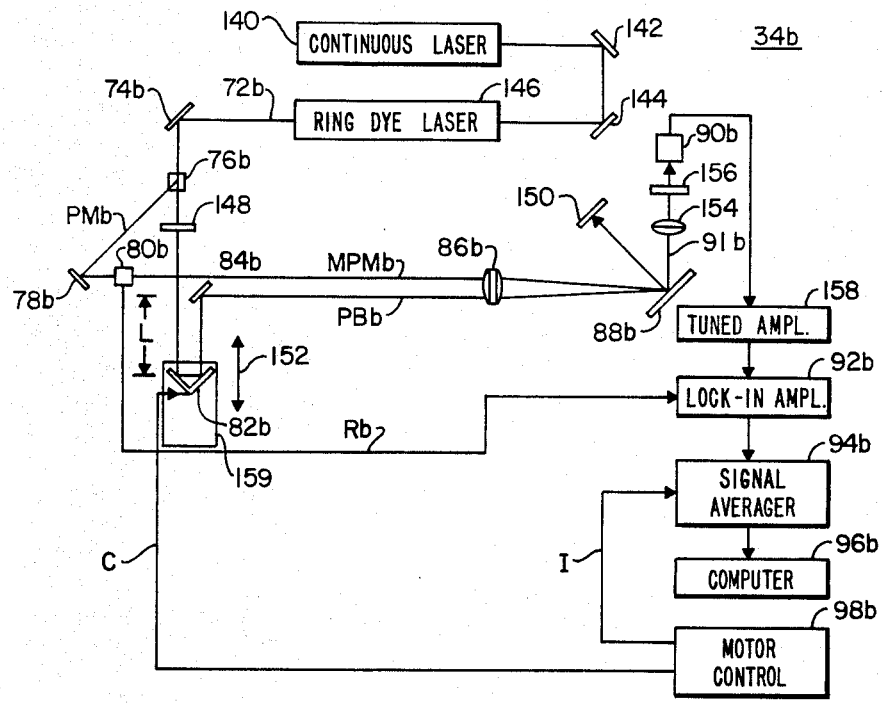
FIG. 5 is a more detailed diagram of the system of FIG. 3.

A more detailed implementation of optical generator/detector system 34b, FIG. 5, includes a continuous wave argon laser 140, such as a Spectra Physics 171, which emits light directed by mirrors 142, 144 to colliding-pulse-modelocking ring dye laser 146, as described by R. L. Fork, B. I. Greene, C. V. Shank, Appl. Phys. Lett. 36, 671 (1981), that generates pulses 72b of light at one direction of polarization. Pulses 72b are directed by mirror 74b through beam splitter 76b which diverts between 50 and 99% of the intensity of pulses 72b as pulsed pump beam PMb. A piece of glass is acceptable for beam splitter 76b. Splitter 76b transmits between 1 and 50% of the intensity of pulse 72b as pulsed probe beam PBb through polarization rotator 148, which rotates the polarization of probe beam PBb by 90°.

Pump beam PMb is directed by mirror 78b through opto-acoustic modulator 80b which uses sound waves to produce 4 MHz oscillations in its crystal to modulate pump beam PMb at that frequency. Modulated pump beam MPMb then passes through lens 86b to film 88b where it is absorbed to generate a stress pulse. The portion of modulated pump beam MPMb that is not absorbed is blocked by beam-blocker 150.

After passing through polarization-rotator 148, probe beam PBb travels to corner cube mirror 82b which is movable relative to mirror 84b to vary path length L. Corner cube 82b is part of translation stage assembly 159, described below. Arrow 152 indicates the directions in which length L is varied. The variations create variable stage time delays for probe beam PBb in relation to pump beam MPMb. Signal I representing time delay is provided to signal averager 94b. Signal averager 94b averages the output of detector 90b while the stage time delay remains set at a particular, predetermined time delay. Translation stage assembly 159 sequentially changes the predetermined time delay, and signal averager 94b, indexed by signal I, successively averages the output of detector 90b.

Reflected probe beam 91b, affected by the returning stress pulse in film 88b, travels through lens 154 and through analyzer 156. The latter improves signal-to-noise ratio by separating light polarized at the direction of polarization of probe beam PBb from light at all other polarization directions, including spurious light from modulated pump beam MPMb. Radiation filtered by analyzer 156 is received by detector 90b, such as a PIN-6D available from United Detector Technology, which outputs an electronic signal to tuned amplifier 158. Amplifier 158 is tuned to the frequency of modulator 80b, 4 MHz in this example. Further processing is provided by lock-in amplifier 92b, such as model 5205 available from Princeton Applied Research, which screens the output of amplifier 158b for both frequency and phase as directed by reference signal Rb.

Figure 6:
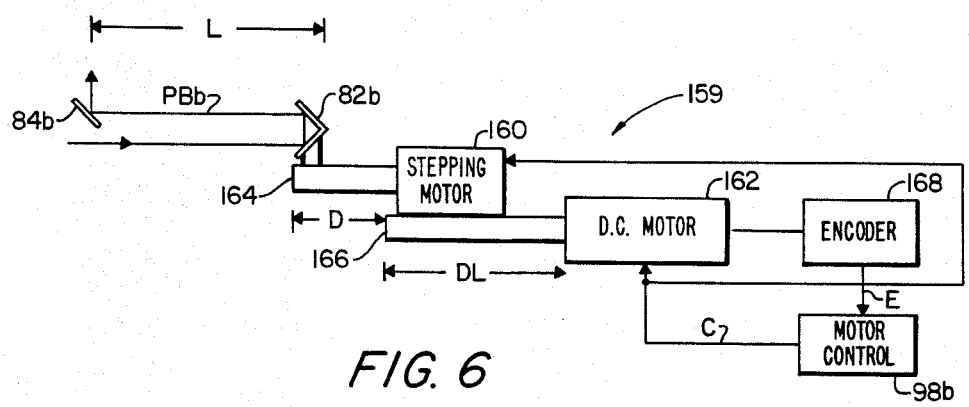
FIG. 6 is a more detailed schematic diagram of the translation stage assembly which varies the path length of the probe beam in FIG. 5.

Time resolution is provided by translation stage 159, FIG. 6. At zero time delay, length L between corner cube 82b and mirror 84b, FIG. 5, is such that a pulse of probe beam PBb impinges at film 88b simultaneously with a pulse of modulated pump beam MPMb. As length L increases, the total path length for probe beam PBb is increased to provide information on reflectivity as a function of stage delay time. For each length L, signal averager 94b, such as model NIC-535, available from Nicolet, Inc. provides an averaged value for probe beam intensities at each stage delay time as described above. After a predetermined period of time, motor control 98b commands a change in length L through signal C. Signal I indicates the new time delay to signal averager 94b, which begins averaging the next set of values. Information is stored in computer 96b for analysis.

Pathlength L between corner cube mirror 82b, which may be a cat's eye mirror, and mirror 84b, FIG. 6, is varied by translation stage assembly 159. Stepping motor 160 provides small adjustments and DC motor 162 provides large adjustments. Pulses of probe beam PBb are delayed by the time required to travel twice the increase in distance L. Stepping motor 160 adjusts stage 164 in direction D while DC motor 162 adjusts larger stage 166 in the direction DL. Motor control 98b receives signal E from encoder 168 indicating the position of large stage 166, and in turn commands adjustment of DC motor 162. Stepping motor 160 is commanded by motor control 98b to advance a predetermined number of steps during each change in pathlength L. Motor control 98b submits to the signal averager signal I representing changes in delay time, resulting from changes in path length L.

Figure 7A:
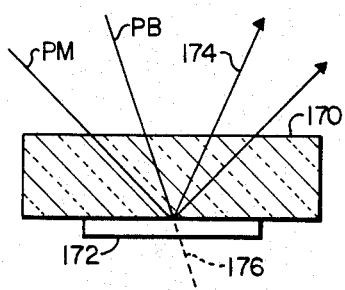
FIGS. 7A-7C illustrate different arrangements of pump beam, probe beam, and film to be examined.
Figure 10:
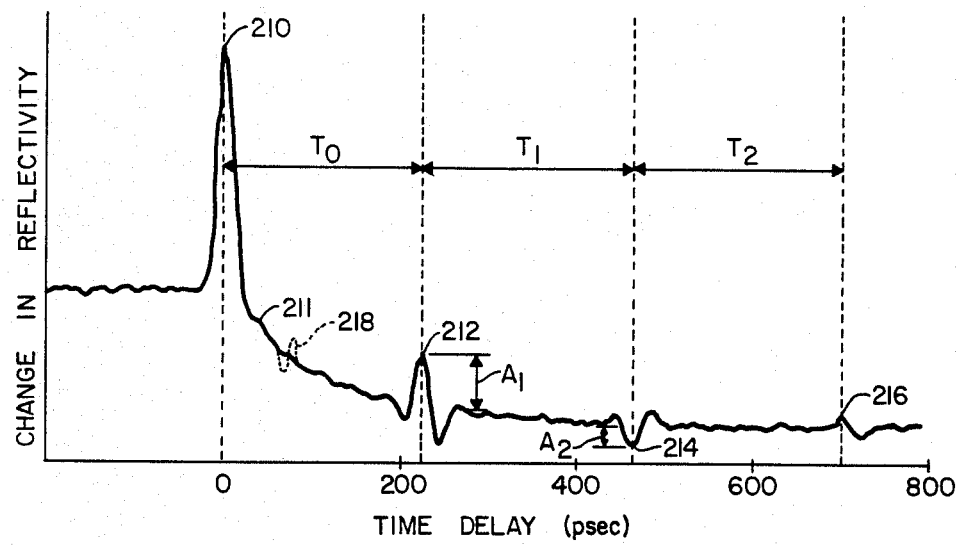
FIG. 10 is a chart of change of intensity of reflected light versus time delay for a probe beam affected by a stress pulse according to this invention.
Figure 11:
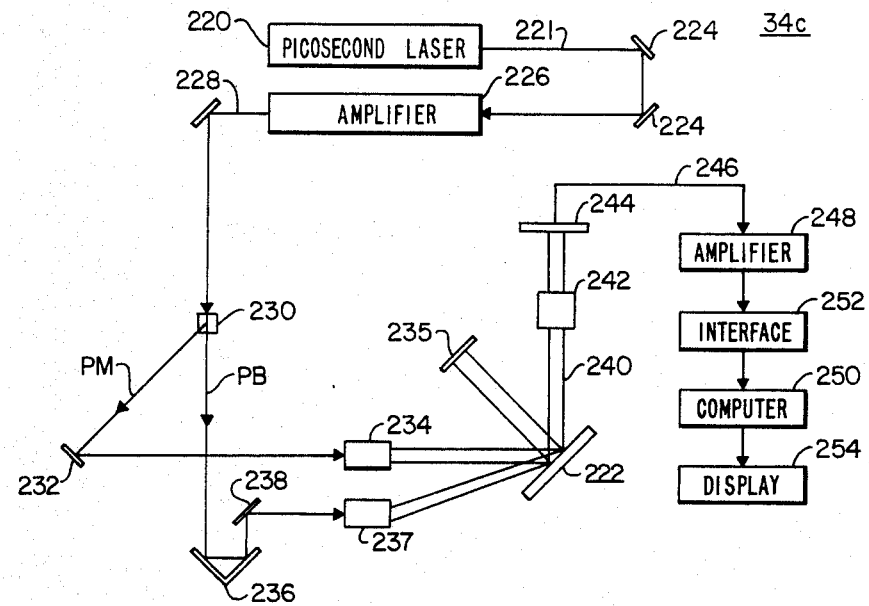
FIG. 11 is a schematic diagram of an optical stress pulse generation and detection system according to this invention which provides a broader lateral view of a film to be examined.

The pump and probe beams can be utilized in several different arrangements in relation to the film to be tested. FIGS. 11A and 1B illustrate pump beam PM absorbed at the upper surface of film 10 and probe beam PB sampling the change in reflectance at the same surface. As shown in FIG. 7A, pump beam PM and probe beam PB may be directed through optically transparent substrate 170 upon optically opaque film 172. The intensity of reflected probe beam 174 is monitored to determine changes of reflectivity. A typical change in reflectivity observed in a thin film of amorphous arsenic telluride $As_2Te_3$ is shown in FIG. 10, described below.

Figure 8:
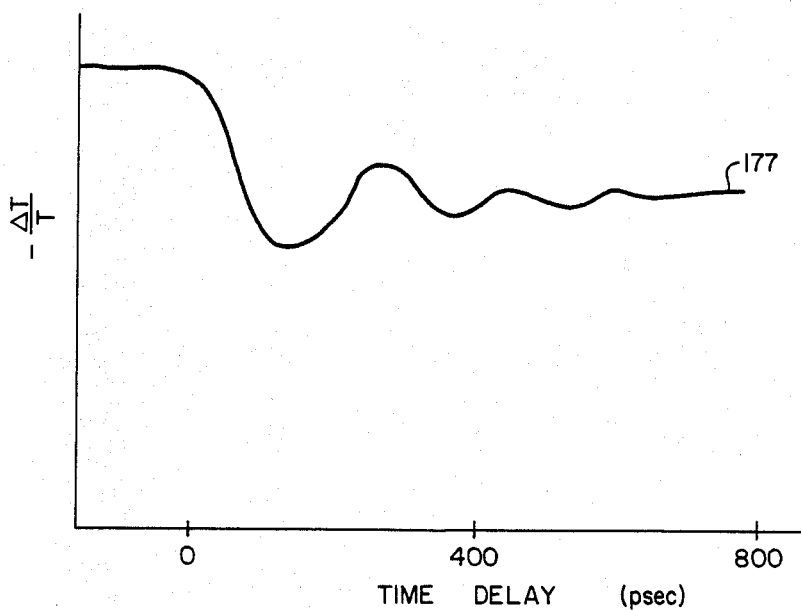
FIG. 8 shows of change of transmission with time for a transmitted probe beam of FIG. 7A.

Alternatively, if film 172 is sufficiently transparent, transmission 176 of probe beam can be monitored. A typical change in transmitted light 176 of probe beam PB, FIG. 7A, over time is illustrated in FIG. 8. When the probe beam is transmitted through a film, the resulting output produces curve 177 as the probe beam is modulated by the stress pulse generated by the pump. See Thomsen, C; Strait, J.; Vardeny, Z; Maris, H. J.; Tauc, J.; and Hauser, J. J., "Coherent Phonon Generation and Detection by Picosecond Light Pulses", Phys. Rev. Lett. 53, 989–992 (1984); see also Thomsen, C; Strait, J.; Vardeny, Z; Maris, H. J.; Tauc, J.; and Hauser, J. J., "Picosecond Optical Generation and Detection of Phonon Waves in a-$As_2$ $Te_3$", AIP Conference Proceedings No. 120, Optical Effects in Amorphous Semiconductors, pp. 102–109 (1984); and Thomsen, C; Strait, J.; Vardeny, Z; Maris, H. J.; Tauc, J.; and Hauser, J. J., "Picosecond Optical Excitation of Phonons in Amorphous $As_2$ $Te_3$", *Ultrafast Phenomena IV*, Ed. D. H. Austron and K. B. Eisenthal (Springer Verlag, N.Y., 1984), pp. 133–136.

Figure 7B:
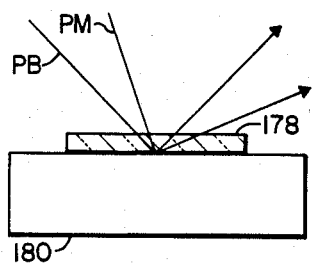
Figure 7C:
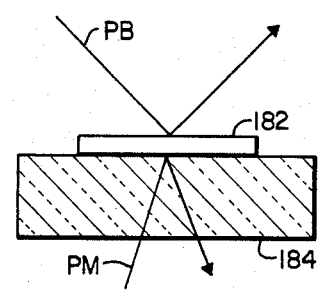

In another arrangement, FIG. 7B, beams PB and PM are directed through transparent film 178 where they are reflected from opaque substrate 180. Part of the induced stress pulse passes to the upper surface of film 178 and then downward through film 178 to affect probe beam PB. Alternatively, probe beam PB may be directed to the side of film 182, FIG. 7C, that is opposite to the side on which pump beam PM is directed. In FIG. 7C, beam PM is directed through transparent substrate 184.

Figure 9:
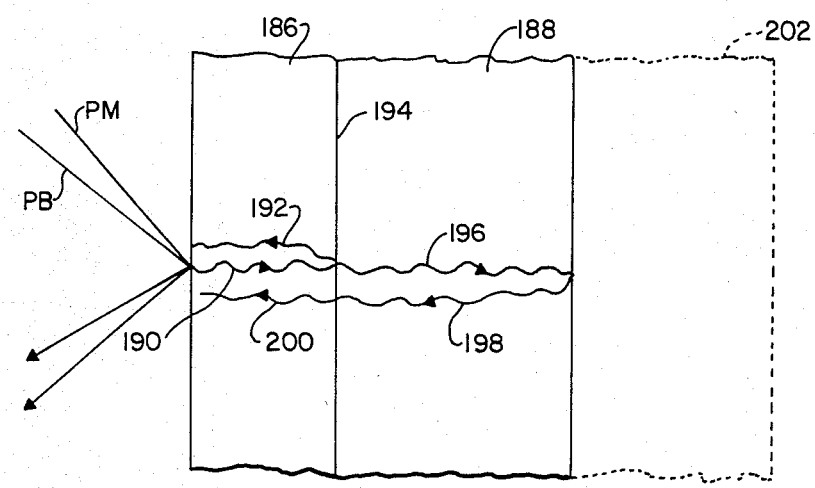
FIG. 9 is an illustration of an active medium used to generate stress pulses in an inactive film to be examined.

Certain films provide little acoustic response when subjected to a pump beam, such as when the films are transparent. These opto-acoustically inactive films may be studied using a film of an opto-acoustically active medium such as amorphous arsenic telluride ($As_2Te_3$). As shown in FIG. 9, active medium 186 is deposited as a thin film on inactive medium 188. Active film 186 serves as a transducer which generates acoustic stress pulses 190 when subjected to pump beam PM. A portion of stress pulse 190 is reflected back as stress pulse 192 at boundary 194 between active film 186 and inactive film 188. Stress pulse 196, the remainder of stress pulse 190, enters inactive medium 188 where some or all of the stress pulse is reflected back as stress pulse 198. Reflected pulse 198 re-enters active medium 186 as stress pulse 200 where it changes the reflectivity of probe beam PB. Multiple reflections are not shown. Inactive film 188 may in turn be deposited upon substrate 202. Since film 188 is observed by impinging pump beam PM and probe beam PB upon active medium 186, impingement on, or through, substrate 202 is not required. Substrate 202 may therefore be an optically impenetrable material such as steel.

Intensity of the reflected probe beam as a function of stage delay time, where signal averager 94b, FIG. 5, provides an average value for each selected time delay, is plotted and extrapolated to produce a curve such as shown in FIG. 10 for a thin film of amorphous arsenic telluride on a sapphire substrate. The film thickness is 2400 Angstroms. The sharp increase in intensity before point 210 and the sharp decrease afterward to approximately point 211 are attributable primarily to processes other than returning stress pulses. For example, the surface of the film changes in reflectivity as the film is heated. The effect on reflectivity diminishes rapidly as heat dissipates into the film. The duration of these transient effects is different for films of different composition. For semiconductor films, absorption of the pump pulse excites electrons in the film; this effect also contributes to changes in reflectivity. The changes in intensity 212, 214, 216 represent portions of the stress pulse returning to the upper surface.

The plot of intensity versus time delay reveals a number of physical properties of a film. The sound velocity can be calculated from $$v = 2d/T_0 \qquad (1)$$

where d is the film thickness and $T_0$ is the time taken for the stress pulse to travel through the film, reflect off the substrate, and return to the surface as shown in FIGS. 1A and 1B. For the arsenic telluride film shown in FIG. 10, $T_0$ is determined by measuring the time delay between zero time delay 210 and valley 212. Alternatively, if the sound velocity is known, time $T_0$ can be used to find the film thickness by solving equation (1) for d.

The velocity of high-frequency sound waves in liquids is measurable by placing a thin film of liquid over a substrate, covered with an opto-acoustically active film such as arsenic telluride, and measuring velocity using one of several methods. For a layer of known thickness equation (1) is used. Another method uses the change in amplitude $A_1$, FIG. 10, measured initially without the liquid when the liquid is placed on top of the opto-acoustically active film. This change in intensity provides the acoustic reflection coefficient $r_{LF}$ at the interface between the liquid and the opto-acoustically active film. Velocity $c_L$ of the liquid is determined from the relationship $$r_{LF} = \frac{\rho_L c_L - \rho_F c_F}{\rho_L c_L + \rho_F c_F} \qquad (2)$$

where $r_{LF}$ is the reflection coefficient, $\rho_L$ and $\rho_F$ are the known densities of the liquid and the opto-acoustically active film, respectively, and $c_F$ is the known velocity of sound in the opto-acoustically active film.

Sound attenuation is determined by measuring the amplitude of the stress pulse after it has traveled repeated distances through the film. During time $T_1$, the induced stress pulse makes a second pass through the film and returns to the surface to generate peak 214. The third pass through the film occurs during $T_2$, ending at valley 216. The ratio of the amplitudes $A_2$ to $A_1$ in FIG. 10 is:

$$\frac{A_2}{A_1} = r_{FS} e^{-2\alpha d} \qquad (3)$$

where $\alpha$ is the attenuation per unit distance, d is the thickness of the film, and $r_{FS}$ is the reflection coefficient of the pulse at the interface between the film and the substrate. Equation (3) can then be solved for $\alpha$ when the reflection coefficient $r_{FS}$ is known. On the other hand, when the attenuation $\alpha$ is known, or is negligible, equation (3) can be used to determine $r_{FS}$. If it is desired to determine both $\alpha$ and $r_{FS}$, the ratio of $A_2$ to $A_1$ is measured for a series of films of different thickness.

The quality of the bonding between the film and the substrate can be determined from measurement of the reflection coefficient $r_{FS}$ of the stress pulse at the boundary between the film and the substrate as just described. If the film is perfectly bonded to the substrate $r_{FS}$ can be calculated from the equation:

$$r_{FS} = \frac{\rho_F c_F - \rho_S c_S}{\rho_F c_F + \rho_S c_S} \qquad (4)$$

where $\rho_F$ and $\rho_S$ are the densities of the film and the substrate, and $c_F$ and $c_S$ are the sound velocities in the film and the substrate. Any difference between the measured $r_{FS}$ and the theoretical value calculated from Equation (4) is an indication of poor bonding of the film to the substrate.

Inhomogeneities including defects, cracks, voids or enclosures in the film will cause signals such as those indicated by dashed line 218. The stress pulse produced by the pump beam scatters off the inhomogeneity, producing an additional stress pulse, which returns to the film surface before time $T_o$. This causes distortion 218. If the inhomogeneity consists of a very thin surface layer (thickness 50 Angstrom, for example) of different acoustic properties on top of the main film, this is seen as a change in shape of signals 212, 214, 216 in FIG. 10.

Optical stress pulse generation and detection systems according to this invention are not limited to simple films. Such a system can be used to obtain information about layer thicknesses and interfaces in superlattices, multi-layer thin-film structures, and other inhomogeneous films.

The above properties are measured by observing changes in reflected or transmitted probe beam intensity or in stress pulse travel time over a range of delay times during one or more reflections of a stress pulse between the upper surface of the film and the film-substrate boundary. Defects and inhomogeneities may also be measured by observing the reflected or transmitted probe beam at one or only a few delay times as the film is translated in relation to the pump beam and the probe beam. Observation at a single delay time can provide a non-destructive, two-dimensional view of a large lateral portion of the film at a fixed depth; the depth that is viewed is dependent upon the delay time between the pump beam and the probe beam. Using sequential time delays, a three-dimensional view of the film is achieved. The scanning of the pump and probe beams over successive narrow areas, as small as 1 micron by 1 micron, produces intensities of the reflected or transmitted probe beam which are plotted as a function of the coordinates of the probe position.

Alternatively, the area of impingement of pump and probe beams may be large in area such that a relatively broad lateral area of a film is viewed simultaneously. Optical stress pulse generation and detection system 34c, FIG. 11, views an area of film 222 which may be as large as 1 cm². Laser 220 produces pulses 221, having a duration of 0.01 to 100 psec, which are directed by mirrors 224 through amplifier 226. Pulses 228, amplified to an energy per pulse of 0.1 mJoule, are passed through beam splitter 230 to produce pulsed pump beam PM and pulsed probe beam PB. Pump beam PM pass through beam expander 234, and onto the part of the surface of film 222 which it is desired to study. The reflected pump beam pulses are absorbed by the beam-block 235. The probe beam pulses PB having a delay established by mirrors 236 and 238 proceed through beam expander 237, which projects them onto the part of the film 222 which is illuminated by the pump. The reflected portion 240 of the probe beam PB is projected by beam expander 242 onto the detector array 244. Model 338, available from Spectra Physics, is acceptable for beam expanders 234, 237 and 242. Detector array 244 is an area detector, such as Model No. RA128×128-1 available from EG&G Reticon; alternatively, detector 244 is a TV camera. Signal 246 representing the intensity of reflected probe beam 240 is passed through amplifier 248 and the interface 252 into computer 250. Computer 250 displays an image of the inspected area in display 254. Different time delays between the probe and pump pulses provide information about inhomogeneities or defects at different depths in film 222.

Viewing a large lateral area of a film at a certain depth is especially useful for examining the bonding of the film to a substrate. The strength of the returning stress pulse, an echo from the interface, indicates the strength of the bonding as described above. The strength of the returning echo is plotted over the lateral area of the film; a poor bonding produces a change in echo amplitude.

Figure 12:
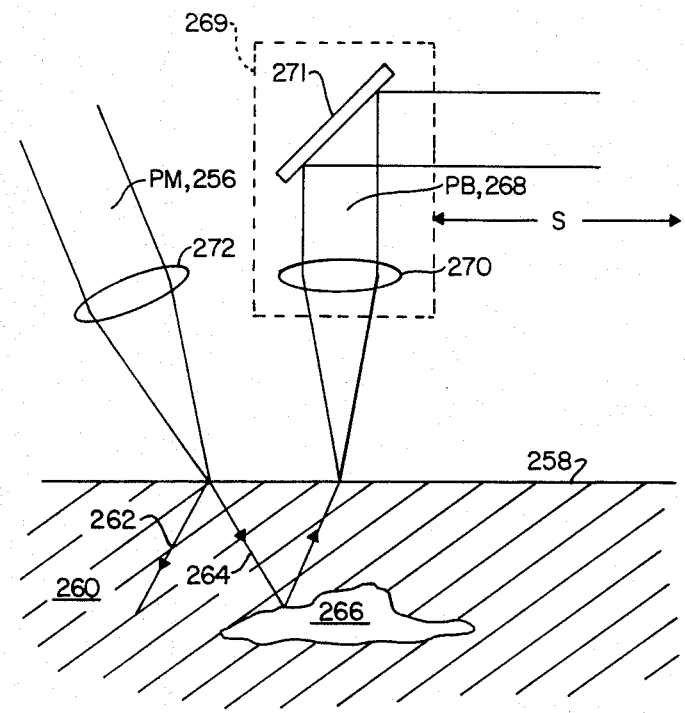
FIG. 12 is an illustration of a mobile probe beam used to examine lateral propagation of a stress pulse.

In another application of an optical stress pulse generation and detection system according to this invention, propagation of stress pulses along a direction parallel to the surface of a film is observed by moving the probe beam in relation to the pump beam over the surface of the film as depicted in FIG. 12. Pump beam pulses 256 are directed upon a single portion of surface 258 of film 260. Pump beam pulses 256 produce stress pulses 262 and 264 which propagate through film 260. A defect such as crack 266 scatters stress pulse 264, providing changes in optical constants of film surface at the location of the probe beam. These changes in optical constants at surface 258 are observed by probe beam pulses 268 as they are scanned in direction S in relation to pump beam 256. The pump and probe beams 256 and 268 pass through separate lenses 272 and 270, and these beams can therefore be scanned separately by moving optical unit 269. Optical unit 269, similar to the optical pickup of a laser-read "compact disk" player, contains lens 270 and mirror 271. When different delay times are used, strain propagation in three dimensions can be reconstructed.

Although specific features of the invention are shown in some drawings and not in others, this is for convenience only as each feature may be combined with any or all of the other features in accordance with the invention.

Other embodiments will occur to those skilled in the are and are within the following claims:

What is claimed is:

1. An optical stress pulse generation and detection system for non-destructively measuring physical properties of a sample, comprising:
   a radiation source for providing a pulsed pump beam having at least one short duration radiation pulse having a duration of 0.01 to 100 psec, and having an intensity and at least one wavelength selected to non-destructively generate a stress pulse in a sample;
   a radiation source for providing a probe beam;
   means for directing said pump beam to a surface of a sample to generate said stress pulse in said sample;
   means for guiding said probe beam to a location at said sample to intercept said stress pulse; and
   means for detecting a change in an optical parameter of said probe beam representative of the change in optical constants induced by said stress pulse in said sample.

2. The optical stress pulse generation and detection system of claim 1 in which said means for detecting includes means for measuring the intensity of said probe beam.

3. The optical stress pulse generation and detection system of claim 2 in which said pump beam and said probe beam are derived from the same source beam having a plurality of short duration pulses and said optical stress pulse generation and detection system further includes beam splitting means for directing a first portion of said source beam to form said pump beam having said plurality of pulses and directing a second portion to form said probe beam having said plurality of pulses.

4. The optical stress pulse generation and detection system of claim 3 in which said source beam has a single direction of polarization.

5. The optical stress pulse generation and detection system of claim 4 further including means for rotating the direction of polarization of said probe beam and means, disposed between said test sample and said means for detecting, for transmitting only radiation at said rotated direction of polarization.

6. The optical stress pulse generation and detection system of claim 3 further including chopper means for modulating said pump beam at a predetermined frequency.

7. The optical stress pulse generation and detection system of claim 6 in which said means for detecting includes amplifier means, responsive to said chopper means, for amplifying only the output of said means for measuring corresponding to said predetermined frequency.

8. The optical stress pulse generation and detection system of claim 3 in which said means for guiding includes means for setting a predetermined time delay between the impingement of a said pulse of said pump beam and a said pulse of said probe beam upon said sample.

9. The optical stress pulse generation and detection system of claim 8 in which said means for detecting includes means for averaging the output of said means for measuring for a plurality of pulse detections while the delay between impingements remains set at said predetermined time delay.

10. The optical stress pulse generation and detection system of claim 9 in which said means for setting sequentially changes said predetermined time delay and said means for averaging successively averages the output of said means for measuring during each successive predetermined time delay setting.

11. The optical stress pulse generation and detection system of claim 3 in which said pump beam receives 50 to 99% of said source beam.

12. The optical stress pulse generation and detection system of claim 11 in which said source beam has an average power of 10 $\mu$W to 1 kW.

13. The optical stress pulse generation and detection system of claim 3 in which said source beam includes wavelengths from 100 Angstroms to 100 microns.

14. The optical stress pulse generation and detection system of claim 1 in which said sample includes a substrate and a film to be examined disposed on said substrate to define a boundary between them.

15. The optical stress pulse generation and detection system of claim 14 in which said film is optically opaque and said pump beam and said probe beam impinge upon the surface of said film opposite said boundary.

16. The optical stress pulse generation and detection system of claim 14 in which said film is optically opaque, said substrate is optically transparent, and said probe beam and said pump beam travel through said substrate to impinge upon said boundary.

17. The optical stress pulse generation and detection system of claim 14 in which said film is optically opaque, said substrate is optically transparent, one said beam travels through said substrate to impinge upon said boundary, and the other said beam impinges upon the surface of said film opposite said boundary.

18. The optical stress pulse generation and detection system of claim 14 in which said film is optically transparent, said substrate is optically opaque, and said pump beam and said probe beam travel through said film to impinge upon said boundary.

19. The optical stress pulse generation and detection system of claim 14 in which said test sample further includes an opto-acoustically active medium disposed on the surface of said film opposite said boundary.

20. The optical stress pulse generation and detection system of claim 19 in which said pump beam and said probe beam impinge upon said active medium.

21. The optical stress pulse generation and detection system of claim 14 in which said substrate is an opto-acoustically active medium.

22. The optical stress pulse generation and detection system of claim 21 in which said pump beam and said probe beam impinge upon the surface of said active medium opposite said boundary.

23. The optical stress pulse generation and detection system of claim 14 in which said film has a thickness from 50 Angstroms to 100 microns.

24. The optical stress pulse generation and detection system of claim 1 in which said probe beam source provides a continuous radiation beam.

25. The optical stress pulse generation and detection system of claim 24 in which said pump beam source provides at least two discrete pump pulses.

26. The optical stress pulse generation and detection system of claim 25 in which said pump beam source provides radiation having an average power of 10 $\mu$W to 1 kW.

27. The optical stress pulse generation and detection system of claim 1 in which said probe beam source provides short duration radiation pulses.

28. The optical stress pulse generation and detection system of claim 27 in which said probe beam source provides probe beam pulses having a duration of 0.01 to 100 psec.

29. The optical stress pulse generation and detection system of claim 1 in which said pump beam includes wavelengths from 10 angstroms to 100 microns.

30. The optical stress pulse generation and detection system of claim 1 in which said pump beam and said probe beam impinge upon the same location at said sample.

31. The optical stress pulse generation and detection system of claim 1 in which said means for directing and said means for guiding include a common lens system for focussing said pump beam and said probe beam onto said sample.

32. The optical stress pulse generation and detection system of claim 1 in which said means for guiding shifts the position of impingement of said probe beam relative to that of said pump beam.

33. The optical stress pulse generation and detection system of claim 1 in which said probe beam is transmitted by said sample.

34. The optical stress pulse generation and detection system of claim 1 in which said probe beam is reflected by said sample.

35. A system for non-destructively measuring physical properties of a sample in which both generation and detection of stress pulses is accomplished optically, comprising:
   a radiation source for providing a pulsed source beam, each pulse having a duration of 0.01 to 100 psec;
   beam splitting means for directing a first portion of said source beam to form a pump beam having an intensity and at least one wavelength selected to non-destructively generate a stress pulse in said sample and directing a second portion to form a probe beam;
   means for directing said pump beam to a surface of said sample to generate said stress pulse in said sample;
   means for guiding said probe beam to a location at said sample to intercept said stress pulse; and
   means for detecting a change in an optical parameter of said probe beam representative of the change in optical constants induced by said stress pulse in said sample.

36. A method for optically and non-destructively generating and detecting the propagation of a stress pulse in a sample, comrpising:
   producing a pulsed pump beam including short duration radiation pulses having a duration of 0.01 to 100 psec, and having an intensity and at least one wavelength selected to non-destructively generate a stress pulse in a sample;
   producing a probe radiation beam;
   directing the pump beam to a surface of the sample to generate said stress pulse in the sample;
   guiding the probe beam to a location at the sample to intercept the stress pulse; and
   detecting the change in optical constants induced by the stress pulse in the sample by measuring the intensity of the probe beam after it intercepts the stress pulse.

37. A method for optically and non-destructively generating and detecting the propagation of a stress pulse in a sample, comprising:
   producing a pulsed source beam having short duration pulses of radiation having a duration of 0.01 to 100 psec;
   diverting a first portion of the source beam to form a pump beam having an intensity and at least one wavelength selected to non-destructively generate a stress pulse in a sample;
   diverting a second portion of the source beam to form a probe beam;
   directing the pump beam to a surface of the sample to generate the stress pulse in the sample;
   guiding the probe beam to a location at the sample to intercept the stress pulse;
   detecting the change in optical constants induced by the stress pulse in the sample by measuring the intensity of the probe beam after it intercepts the stress pulse.

* * * * *